US00PP08368P

United States Patent [19]

Bull

[11] Patent Number: Plant 8,368

[45] Date of Patent: Sep. 7, 1993

[54] IMPATIENS PLANT NAMED MELANIE

[76] Inventor: Norbert Bull, Gärtnersiedlung 2, 2351 Gönnebek, Fed. Rep. of Germany

[21] Appl. No.: 802,849

[22] Filed: Dec. 6, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

An Impatiens plant named Melanie, characterized by its light, almost bluish pink flower color with red-purple center eye, compact growth habit, solid dark green foliage, very early flowering, and its floriferous habit.

2 Drawing Sheets

The present invention relates to a new and distinctive cultivar of Impatiens plant, botanically known as Impatiens, and referred to be the cultivar name Melanie. The new cultivar was developed by me through controlled breeding by crossing seed or female parent identified as Seedling No. 9 with male or pollen parent identified as Seedling No. 3. Both parents are unreleased and propriety lines.

Asexual reproduction of the new cultivar by the inventor by terminal or stem cuttings taken at Gönnebek, Federal Republic of Germany has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Pale bluish pink flower color, with red-purple center eye.
2. Compact growth habit.
3. Very early flowering.
4. Very floriferous habit.
5. Suitable for pot plant, patio, bedding plant, and hanging basket culture.

Melanie has a flower color somewhat similar to the flower color of the cultivar Equinox, disclosed in U.S. Plant Pat. No. 6,297. However, Melanie is more compact, has a different foliage shape, and the underside of its foliage is green rather than red as in Equinox.

The accompanying colored photographs illustrate the overall appearance of this cultivar, showing the colors as true as it is reasonably possible to obtain in a colored reproduction of this type.

The photo at the top of sheet 1 comprises a top perspective view of a potted plant of Melanie.

The bottom photo on sheet 1 shows a single flower (top side), and top and bottom views of a typical leaf. The photograph on sheet 2 shows the upper side and under side of typical flowers, a bud with attached spur, and the upper side and bottom side of typical leaves. Scales in centimeters are included to show the size of these parts.

The following is a detailed description of my new Impatiens cultivar based on plants produced under normal commercial practice at Gönnebek, Federal Republic of Germany.

Color references are made to The Royal Horticultural Society (R.H.S.) Colour Chart except where general terms of ordinary dictionary significance are used.

Parentage: Controlled cross between Bull Unnamed Seedling No. 9×Bull Unnamed Seedling No. 3.

Propagation:

*Type cutting.*—Stem 15–20 mm long will grow to 4–5 cm in 20 days.

*Time to initiate roots.*—8 days at 22° C. summer.

*Time to initiate roots.*—10 days at 20° C. winter.

*Rooting habit.*—Rapid rooting.

Plant description:

*Form.*—Symmetrically mounded, self-branching.

*Habit of growth.*—Compact growth habit. Eight (8) weeks after sticking stem cuttings in 12 cm pots, plant is approximately 30 cm in diameter and 30 cm in height, measured from top of pot.

*Foliage description.*—(1) Size: Relatively small length approximately 9–10 cm, width 3–4 cm at point of maximum width. (2) Shape: Generally ovate, with acute to acuminate tip and rounded to acute base; see photos. (3) Margin: Mildly serrated. (4) Color: (a) Young foliage under surface: Dark green, approximately RHS 139A. (b) Under surface: Light green darker than 191A-B. (c) Mature foliage upper surface: Dark green, RHS 139A. (d) Under surface: Light green approximately 191A-B. (5) Veination: Red veins on under side (see photo). (6) Variegation: None.

Flowering description:

*Flowering habit.*—Flowers from leaf whorl in uniform manner. Flowering is very early; cuttings stuck in jiffy pot for rooting and transferred to 12 cm pot after 4 weeks will flower 7–8 weeks after sticking of cuttings.

*Natural flowering season.*—March until October.

*Flower buds.*—Typical; green to brown-red in color.

*Flowers borne.*—On pedicels.

*Quantity of flowers.*—Very floriferous. Flowers both mask the crown and occur above the leaf canopy.

*Spur.*—Downwardly curved from base of calyx, approximately 4–5 cm in length and red-purple in color (see the photo on sheet 2).

*Longevity.*—Flowers are long lasting and non-fading.

*Petals.*—Number of petals: Five (5). Shape: Generally heart-shaped (see photo). Color: Upper surface: 56A with 61C center eye, and 61C tinging primarily along midvein; color very uniform. Under surface: Same as for top side, only slightly lighter. Size of flower: Medium, approximately 5.5 to 6 cm. in diameter.

*Reproductive organs.*—Stamens: Five (5). Anthers: Hooded, white to red in color. Pollen Color: White.

Stigma: Five in number, white in color. Styles: White in color. Ovary: 5 in number, size 3–5 mm., green in color. Disease resistance: No disease problems noted to date.

I claim:

1. A new and distinct Impatiens plant named Melanie, as illustrated and described.

* * * * *

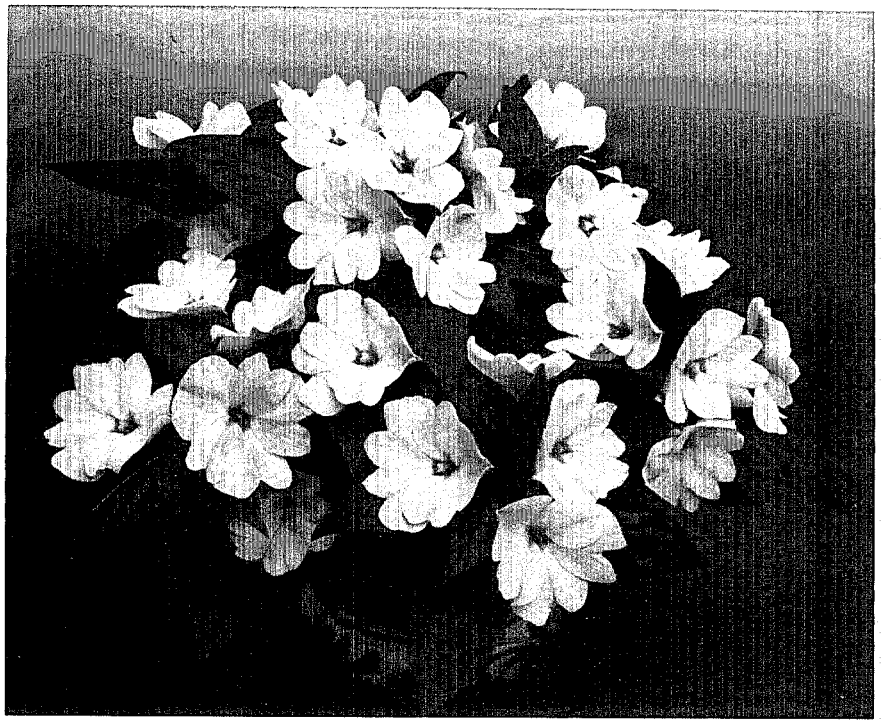
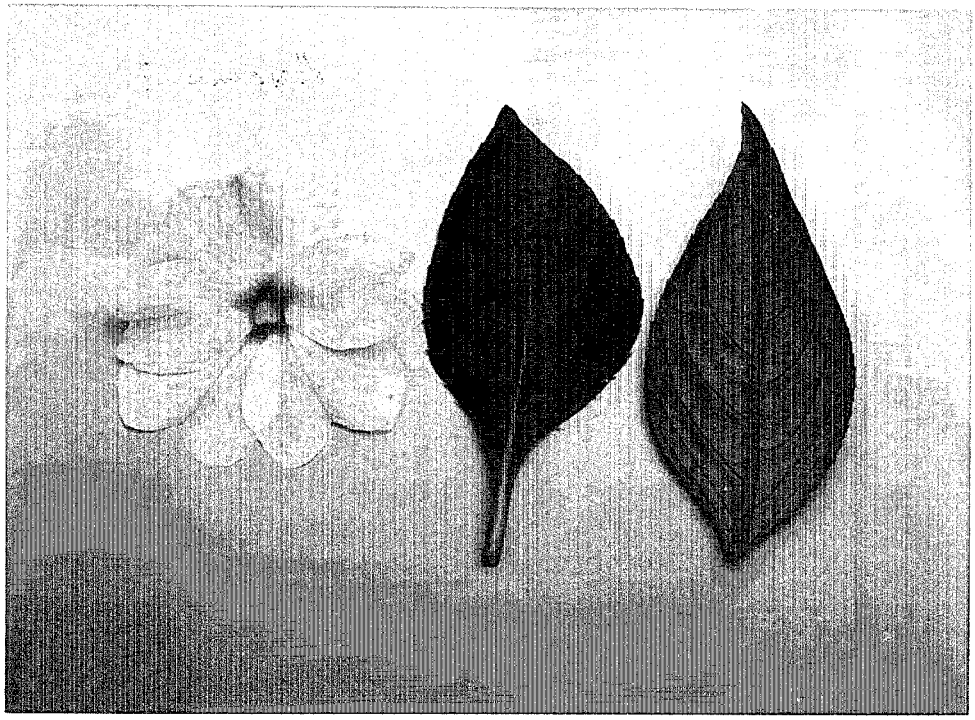

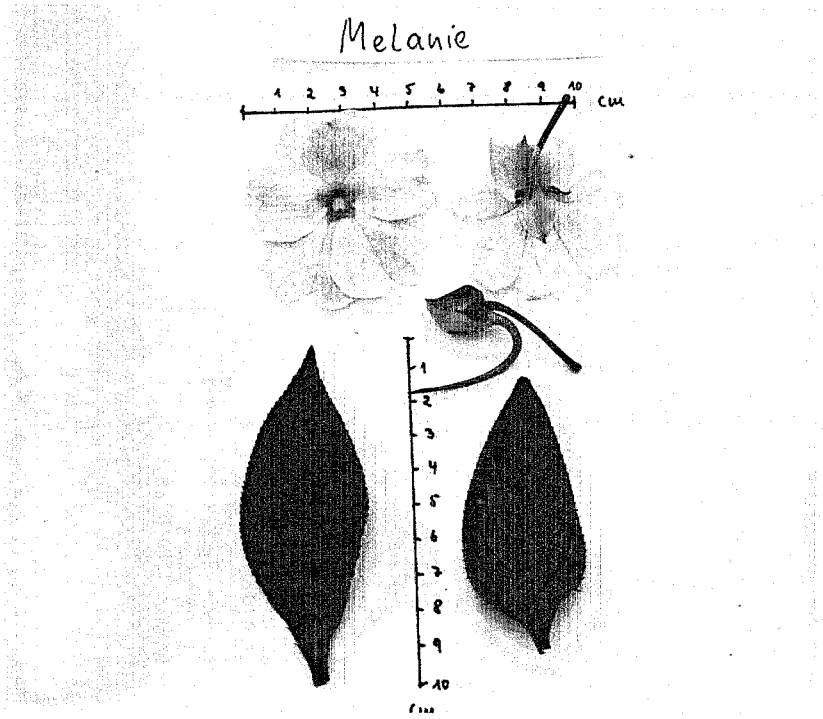
Melanie
1 2 3 4 5 6 7 8 9 10
cm
1
2
3
4
5
6
7
8
9
10